United States Patent
Fischetti

(12) 
(10) Patent No.: US 6,602,507 B1
(45) Date of Patent: Aug. 5, 2003

(54) SYNTHETIC PEPTIDES FROM STREPTOCOCCAL M PROTEIN AND VACCINES PREPARED THEREFROM

(75) Inventor: Vincent A. Fischetti, West Hempstead, NY (US)

(73) Assignee: The Rockefeller University, New York, NY (US)

(*) Notice: Subject to any disclaimer, the term of this patent is extended or adjusted under 35 U.S.C. 154(b) by 0 days.

(21) Appl. No.: 08/369,295

(22) Filed: Jan. 6, 1995

Related U.S. Application Data

(63) Continuation of application No. 08/200,913, filed on Feb. 22, 1994, now abandoned, which is a continuation of application No. 08/068,598, filed on May 28, 1993, now abandoned, which is a continuation of application No. 07/845,865, filed on Mar. 3, 1992, now abandoned, which is a continuation of application No. 07/540,101, filed on Jun. 19, 1990, now abandoned, which is a continuation-in-part of application No. 07/315,588, filed on Feb. 27, 1989, now abandoned, which is a continuation-in-part of application No. 07/173,380, filed on Mar. 25, 1988, now abandoned.

(51) Int. Cl.[7] .................. A61K 39/09; A61K 39/385; C07K 1/00; C07K 7/00
(52) U.S. Cl. .................. 424/244.1; 424/193.1; 424/194.1; 424/236.1; 530/326; 530/328; 530/345; 530/404; 530/405; 530/408; 530/409
(58) Field of Search .................. 530/326, 328, 530/345, 404, 405, 408, 409; 424/193, 194, 236.1, 244.1

(56) References Cited

U.S. PATENT DOCUMENTS 4,695,562 A * 9/1987 Beachey et al. ............ 530/326
4,705,684 A * 11/1987 Beachey ..................... 530/326
4,784,948 A * 11/1988 Scott et al. ................. 435/69.3

OTHER PUBLICATIONS

Kevin Jones et al. "Location of Variable and Conserved Epitopes Among the Multiple Serotypes of Streptococcal M Protein" J. Exp. Med. 161. Mar. 1985. pp 623–628.*
Edwin Beachey et al "Protective and Autoimmune Epitopes of Stretococcal M Proteins" vol., 6. Apr. 1988, pp. 192–196.*
Susan Hollingshead et al "Complete Nucleotide Sequence of Type 6 M Protein of the Group A Streptococcus" J. Biol Chem. 261(4). Feb. 5, 1986. pp. 1677–1686.*
Sara McKenzie et al "Cholera Toxin B Subunit as a Carrier Protein to Stimulate A Mucosal Immune Response" J. of Immun. 133(4). Oct. 1984, pp 1818–1824.*
Jones, et al, J. Exp. Med, vol. 164, pp 1226–1238, 1986.*
J. Exp. Med. vol. 167, 1988, K.F. Jones et al "The importance of the location of antibody binding on the M6 protein for opsonization and phagocytosis of group A M6 streptococci" *Complete Article* pp. 1114–1123.
The Journal of Immunology vol. 141, V.A. Fischetti. et al "Mapping the immunodeterminants of the complete streptococcal M6 protein molecule" 1988. pp. 3592–9.
J. Exp. Med. vol. 164, 1986 K.F. Jones et al. "Immunochemical localization and amino acid sequences of cross-reactive epitopes within the group A streptococcal M6 protein" *Complete Article* pp 1226–1238.

* cited by examiner

*Primary Examiner*—Ponnathapu Achutamurthy
(74) *Attorney, Agent, or Firm*—Burns, Doane, Swecker & Mathis, L.L.P.

(57) ABSTRACT

Synthetic polypeptides from the conserved exposed region of streptococcal M protein are useful to prepare vaccines for oral or intranasal administration which will protect against streptococcal infection.

11 Claims, 4 Drawing Sheets

|  |  | a | b | c | d | e | f | g |
|---|---|---|---|---|---|---|---|---|
| 1 | Arg Val Phe Pro Arg Gly Thr Val Glu Asn Pro | | | | | | | |
| 12 | | | Asp | Lys | Ala | Arg | Glu | Leu |
| 18 | | Leu | Asn | Lys | Tyr | Asp | Val | Glu |
| 25 | | Asn | Ser | Met | Leu | Gln | Ala | Asn |
| 32 | | Asn | Asp | Lys | Leu | Thr | Thr | Glu |
| 39 | | Asn | Asn | Asn | Leu | Thr | Asp | Gln |
| 46 | | Asn | Lys | Asn | Leu | Thr | Thr | Glu |
| 53 | | Asn | Lys | Asn | Leu | Thr | Asp | Gln |
| 60 | | Asn | Lys | Asn | Leu | Thr | Thr | Glu |
| 67 | | Asn | Lys | Asn | Leu | Thr | Asp | Gln |
| 74 | | Asn | Lys | Asn | Leu | Thr | Thr | Glu |
| 81 | | Asn | Lys | Glu | Leu | Lys | Ala | Glu |
| 88 | | Glu | Asn | Arg | Leu | Thr | Thr | Glu |
| 95 | | Asn | Lys | Gly | Leu | Thr | Lys | Lys |
| 102 | | Leu | Ser | Glu | Ala | Glu | Glu | Glu |
| 109 | | Ala | | | | | | |
| 110 | | Ala | Asn | Lys | Glu | Arg | Glu | Asn |
| 117 | | Lys | Glu | Ala | Ile | Gly | Thr | Leu |
| 124 | | Lys | Lys | Thr | Leu | Asp | Glu | Thr |
| 131 | | | | | Val | Lys | Asp | Lys |
| 135 | | Ile | Ala | Lys | Glu | Gln | Glu | Ser |
| 142 | | Lys | Glu | Thr | Ile | Gly | Thr | Leu |
| 149 | | Lys | Lys | Thr | Leu | Asp | Glu | Thr |
| 156 | | | | | Val | Lys | Asp | Lys |
| 160 | | Ile | Ala | Lys | Glu | Gln | Glu | Ser |
| 167 | | Lys | Glu | Thr | Ile | Gly | Thr | Leu |
| 174 | | Lys | Lys | Thr | Leu | Asp | Glu | Thr |
| 181 | | | | | Val | Lys | Asp | Lys |
| 185 | | Ile | Ala | Lys | Glu | Gln | Glu | Ser |
| 192 | | Lys | Glu | Thr | Ile | Gly | Thr | Leu |
| 199 | | Lys | Lys | Ile | Leu | Asp | Glu | Thr |
| 206 | | | | | Val | Lys | Asp | Lys |
| 210 | | Ile | Ala | Arg | Glu | Gln | Lys | Ser |
| 217 | | Lys | Gln | Asp | Ile | Gly | Ala | Leu |
| 224 | | Lys | Gln | Glu | Leu | Ala | Lys | Lys |

FIG. 1A

```
231                               Asp Glu Gly
234     Asn Lys Val Ser Glu Ala Ser
241     Arg Lys Gly Leu Arg Arg Asp
248     Leu Asp Ala Ser Arg Glu Ala
255     Lys Lys Gln Val Glu Lys Asp
262     Leu Ala Asn Leu Thr Ala Glu
269     Leu Asp Lys Val Lys Glu Glu
276     Lys Gln Ile Ser Asp Ala Ser
283     Arg Gln Gly Leu Arg Arg Asp
290     Leu Asp Ala Ser Arg Glu Ala
297     Lys Lys Gln Val Glu Lys Ala
304     Leu Glu Glu Ala Asn Ser Lys
311     Leu Ala Ala Leu Glu Lys Leu
318     Asn Lys Glu Leu Glu Glu Ser
325     Lys Lys Leu Thr Glu Lys Glu
332     Lys Ala Glu Leu Gln
337         Ala Lys Leu Glu Ala Glu
343     Ala Lys Ala Leu Lys Glu Gln
350     Leu Ala Lys Gln Ala Glu Glu
357     Leu Ala Lys Leu Arg Ala

363     Gly Lys Ala Ser Asp Ser Gln Thr
371     Pro Asp Ala Lys
375     Pro Gly Asn Lys Val Val
381     Pro Gly Lys Gly Gln Ala
387     Pro Gln Ala Gly Thr Lys
393     Pro Asn Gln Asn Lys Ala
399     Pro Met Lys Glu Thr Lys Arg Gln Leu
408     Pro Ser Thr Gly Glu Thr Ala Asn Pro

417     Phe Phe Thr Ala Ala Ala Leu
424     Thr Val Met Ala Thr Ala Gly
431     Val Ala Ala Val Val

436     Lys Arg Lys Glu Glu Asn
```

FIG. 1B

SYNTHETIC PEPTIDES FROM STREPTOCOCCAL M PROTEIN AND VACCINES PREPARED THEREFROM

RELATED APPLICATIONS

This application is a continuation of application Ser. No. 08/200,913, filed Feb. 22, 1994, which was a continuation of application Ser. No. 08/068,598, filed May 28, 1993, which was a continuation of application Ser. No. 07/845,865, filed Mar. 3, 1992, which was a continuation of application Ser. No. 07/540,101, filed Jun. 19, 1990, which was a continuation-in-part of application Ser. No. 07/315,588, filed Feb. 27, 1989, which was a continuation-in-part of application No. 07/173,380, filed Mar. 25, 1988 all abandoned.

This invention relates to polypeptides and vaccines and conjugates therefrom as well as to methods for controlling streptococcal infection.

BACKGROUND OF THE INVENTION

The M protein of group A streptococci is a fibrous dimer of helices arranged in a coiled coil extending about 50 nm from the surface of these organisms. It is a filbrillar molecule of which there exists more than 80 serological types. M protein renders the streptococcus resistant to nonimmune phagocytosis. It is the major virulence factor of streptococcal bacteria.

SUMMARY OF THE INVENTION

It has now been surprisingly found that polypeptides from the conserved region of the M protein elicit a protective immune response when administered to a mammal in need of protection against streptococcal infection.

The present invention thus provides a polypeptide which elicits an immune response in a mammal on administration to said mammal which comprises an amino acid sequence containing at least 5 amino acid residues, said sequence being the same or substantially the same as a sequence of amino acid residues in the conserved exposed region of the M protein of group A streptococci.

The present invention also provides an antigen conjugate which elicits an immune response in a mammal on administration to said mammal which comprises a linkable carrier covalently linked to a polypeptide which comprises an amino acid sequence containing at least 5 amino acid residues, said sequence being the same or substantially the same as a sequence of amino acid residues in the conserved exposed region of the M protein of group A streptococci.

The present invention further provides a method of controlling streptococcal infection in a mammal in need of such control which comprises intranasal or oral administration to said mammal of a polypeptide which comprises an amino acid sequence containing at least 5 amino acid residues said sequence being the same or substantially the same as a sequence of amino acid residues in the conserved exposed region of the M protein of group A streptococci in an amount which is sufficient to stimulate the production of a streptococcal infection controlling quantity of immunoglobulin.

In addition, the present invention provides a vaccine to protect against streptococcal infection which comprises a biologically acceptable diluent and a polypeptide, said polypeptide comprising an amino acid sequence containing at least 5 amino acid residues, said sequence being the same or substantially the same as a sequence of amino acid residues in the conserved exposed region of the M protein of group A streptococci said polypeptide being present in an amount which is sufficient to stimulate the production of sufficient immunoglobulin to elicit such protection.

Furthermore, the present invention provides certain polypeptides comprising specific sequences from the conserved exposed region of the M protein of group A streptococci.

The term "the same or substantially the same" is used herein to describe the sequence of amino acids in the polypeptides having the desirable activity because such polypeptides are either identical to a segment from the exposed conserved region of the M protein of group A streptococci or so similar to the segment that it has the same activity. No undue experimentation is required to determine polypeptides which are so similar to a segment from the exposed conserved region of the M protein that they have the same activity as those which are the same as the segment. The skilled artisan, from reading this specification can prepare homologous polypeptides having the same activity and substantially the same sequence as a segment from the exposed conserved region of the M protein. For instance, the termini may be extended, e.g., to provide an anchor to bind the polypeptide to a binder or carrier molecule. A polypeptide with the same activity and a high degree of homology with a sequence from the conserved, exposed region might be synthesized more readily or be less expensive to prepare, and, this polypeptide is considered within the scope of this invention. The exact sequence of the M protein segment is not essential to the practice of this invention so long as it has the desired activity.

To similarly clarify the terms used herein, the polypeptides of the present invention are not the entire M protein, but rather, have the same, or substantially the same amino acid sequence as a segment from the conserved, exposed region of the M protein of group A streptococci. The polypeptides of this invention are not considered to be naturally occurring. To obtain the polypeptides of this invention, selective enzymatic or chemical cleavage from the M protein can be employed, although synthesis, e.g., solid phase synthesis, is preferred. Thus, the polypeptides employed in this invention are not naturally occurring polypeptides because, even if isolated from the M protein, they are pure or substantially pure polypeptides or are purer than the M protein. In any event, the polypeptides herein, even if isolated from the M protein, are not products of nature because the polypeptides herein are not the entire M protein, but are the same or substantially the same as an amino acid sequence from a segment of the M protein, the conserved exposed region.

Furthermore, as detailed below, the polypeptides of this invention do not have the same characteristics and utility as any M protein or other naturally occurring protein, because the native M protein cannot be utilized to protect against streptococcal infections by different streptococcal zenotypes because of species variability of the M protein found in different strains of streptococci, whereas the polypeptides of this invention can be used to prepare vaccines affording broad protection which is not strain specific. Thus, the polypeptides of this invention are not products of nature as they do not exist as distinct entities of nature and have never before been produced, and because no product of nature has the same properties as these polypeptides.

BRIEF DESCRIPTION OF DRAWINGS

FIG. 1 shows complete amino acid sequence of the M6 protein from strain D471 of group A streptococcal culture from The Rockefeller University collection.

DETAILED DESCRIPTION

Figure 2:
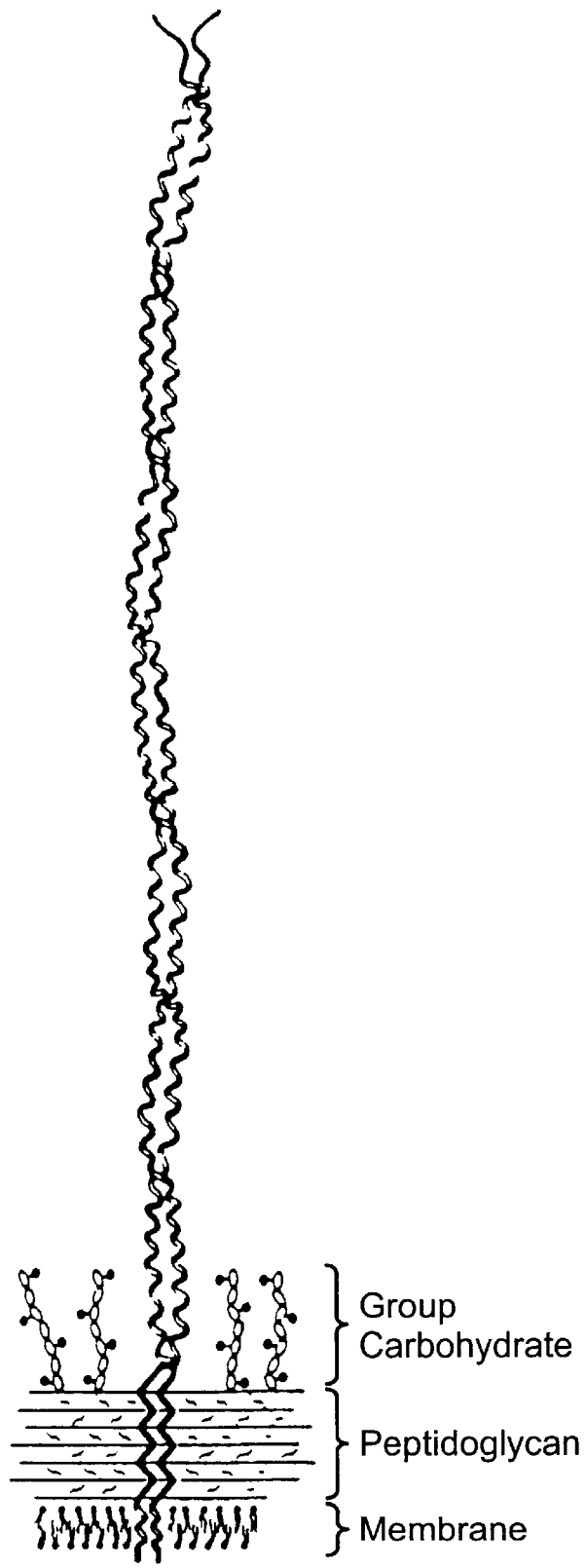
FIG. 2 illustrates a model of the complete M6 protein from strain D471 as it exists on the cell wall.

It will be seen from FIG. 2 that a portion of the M protein, the carboxy terminus, is embedded in the peptidoglycan and membrane of the cell wall. The adjacent segment is sheltered by the carbohydrate of the cell wall which is composed of a rhamnose backbone (open circle) and N-acetylglycosamine branches (closed circles). The distal amino terminus of the M-protein is non-helical. There is an exposed region between the carbonhdrate shelter and the non-helical region.

FIG. 1 is the complete amino acid sequence of an M protein from a specific strain. M proteins from other strains will have generally the same structural features and conformation, but the amino acid sequences will vary. The principal variations occur towards the amino terminal. The molecules become more and more conserved towards the carboxy end. Thus homology within M molecules of different serotypes progressively increases at sites which are closer to the carboxy terminus and more proximal to the cell wall.

It is the variability at the amino terminus which is responsible for the antigenic variation of the M protein. Antibodies which afford protection against one serotype are not effective to resist infection by other serotypes in an opsonophagocytosis assay. Thus, it is theoretically possible for an individual to be infected many times with different streptococcal strains, and each infection will continue until the immune system has generated a sufficient concentration of antibodies to the variable region to neutralize the specific infecting strain.

Figure 3:
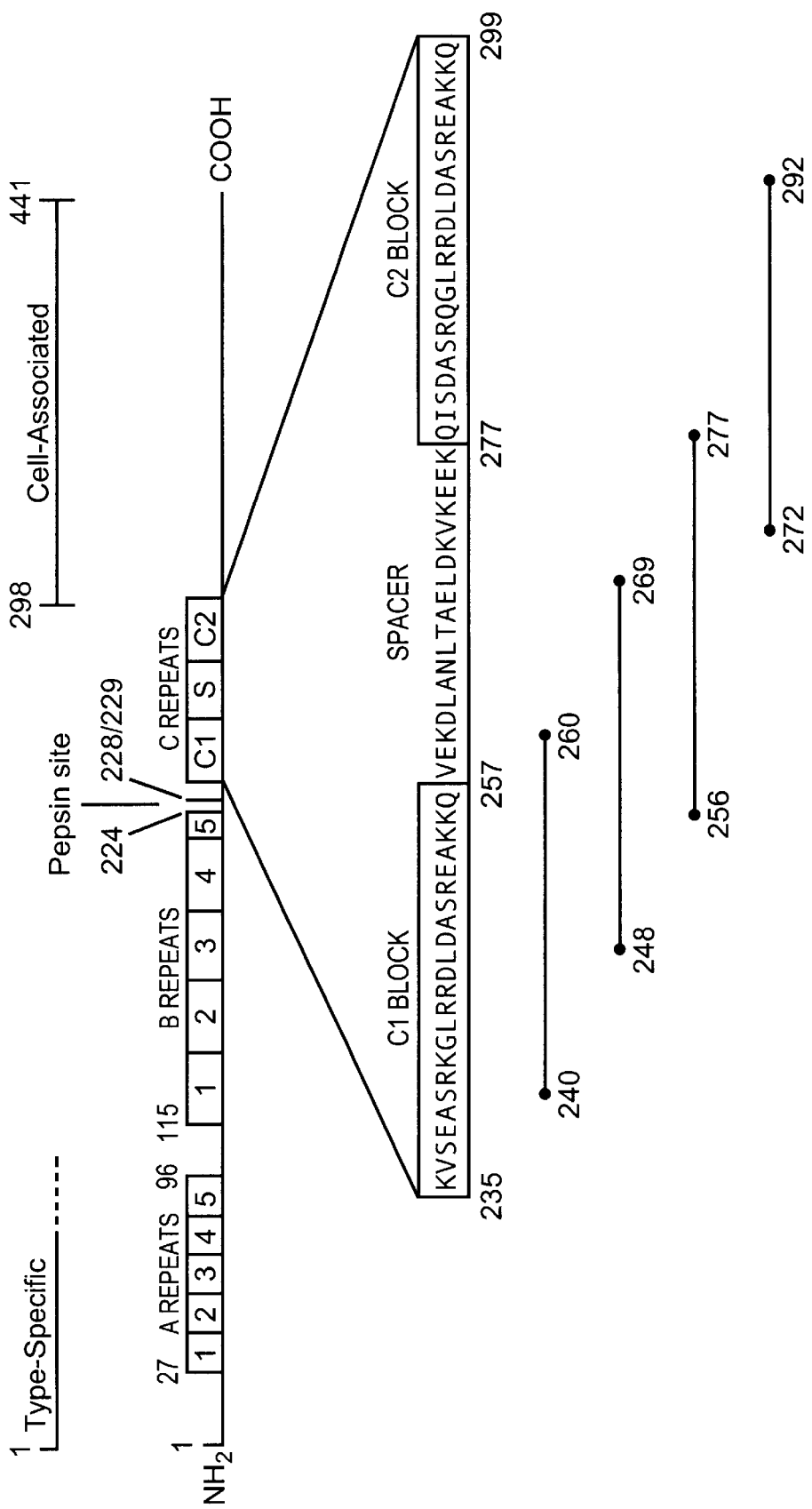
FIG. 3 illustrates the location of the preferred conserved region peptides.

In particular, FIG. 3 shows that the amino end of M protein is type specific (antigenically variable). Sequences 298-441 are generally cell associated. Within the conserved region occurs the C repeats composed of the C1 block, Spacer and C2 Block. The non-type-specific epitopes of M6 which are shared among other M protein serotypes to varying degrees are located here. Monoclonal and affinity-purified antipeptide antibodies which map to the B repeat region and pepsin site of M6 protein are shared among only 10% to 17% of more than 50 distinct serotypes. In contrast, antibodies which map to the adjacent C repeat region are shared among approximately 60 to 70% of the serotypes. While polypeptides herein can extend from the B5 repeat Block through the C repeat region and even from the B4 repeat Block to the carboxy terminus, for broad-based protection, it is preferred that the polypeptides be the same or substantially similar to the conserved exposed region which runs from about position 170 to position 299, and it is even more preferred that the polypeptides be the same or substantially similar to the region which runs from about position 235 to position 299; i.e., completely contained within the highly conserved C repeat region.

Group A streptococci are widespread human pathogens which are responsible for nasopharyngeal infections and impetigo. There are over 25 million cases of group A streptococcal infections each year in the United States alone. Despite the fact that streptococcal infection can be successfully treated with antibiotics, in the interim it often causes significant discomfort and loss in productivity. A small percentage of infected individuals afflicted with streptococcal infection develop a more serious illness such as rheumatic fever and glomerulonephritis. In developing countries, rheumatic fever is the leading cause of heart disease among children. Thus, there is a strong impetus to develop a safe and effective vaccine against group A streptococci.

Experience shows, however, that streptococcal infections are generally limited to children, peaking at age 7. Adults are generally resistant to such infections, presumably because they have built up an immunity which is effective against most serotypes. Hence, there may be an immunological response to streptococcal infection which produces antibodies which recognize epitopes on most, if not all streptococcal serotypes. However, there are over 80 distinct serotypes such that a vaccine based on type-specific epitopes may not be practical.

It has now been discovered that epitopes offering broad protection are in the conserved region of the M protein which is not protected by its proximity to the cell wall, i.e., the conserved, exposed region of the M protein. While the identity of the amino acids in this region varies somewhat amongst serotypes, it generally runs from about position 170 to position 299 on the M protein molecule, preferably from about position 235 to position 299.

Polypeptides from that region are capable of eliciting and do elicit a protective immune response when administered to a mammal in need of protection against streptococcal infection.

As is known, the mammalian body has several methods for protecting itself against infection by microorganisms. One is the adaptive system in which the immune response to an invading organism results in the production of IgG antibodies which function by allowing opsonization and phagocytosis mediated by complement. Another is the production or activation of IgA which is the predominant immunoglogulin of seromucous secretions such as saliva, tracheobronchial secretions, colostrum, milk and genitourinary secretions. IgG is also found in these secretions but in a lesser concentration. Secretory IgA (sIgA) is a dimeric form of IgA protected from proteolysis by the secretory component. One of the functions of IgA is to prevent infective microorganisms from adhering, colonizing and invading the mucous tissue.

The presently preferred procedure for the practice of this invention involves principally the stimulation of the secretory immune system, particularly sIgA by intranasal or oral administration of polypeptide antigens. There may be concomitant production of IgG, and both may contribute to the immunization. The invention will be described principally as applied to that procedure. The polypeptides of the invention may also be used to stimulate IgA as the principal response by parenteral administration with concomitant production of low level IgA.

The polypeptides used in the invention are selected from polypeptides in the conserved exposed section of the M protein. Generally they will contain at least 5 amino acid residues and will be administered as haptens conjugated to a carrier. Generally, it is impractical for the polypeptide to contain more than 25 amino acid segments because the synthesis of synthetic peptides becomes more difficult as the number of amino acid residues in the peptide increases.

The polypeptide can be obtained by selective enzymatic or chemical cleavage from the M protein, but it is far more preferable to synthesize the selected polypeptide using any of the known techniques, e.g., the solid phase Merrifield synthesis where the peptide is synthesized on a resin substrate, separated and purified. Utilizing this procedure, polypeptides having the exact sequence of amino acids from the selected site on the conserved exposed section of the M protein can be produced. However, it is not essential that an exact sequence be employed. Minor modifications, especially those that do not change the conformation of the peptide can be made by substituting one or more amino acids to produce useful polypeptides having substantially the same sequence as a segment of the conserved exposed region in the M protein. However, the sequence of the polypeptide will usually have the same sequence as a segment of the conserved exposed region in the M protein.

It may also be desirable to add one or several amino acids to either terminus of the selected polypeptide. This variation of the invention will be typically employed to bind the polypeptide to a carrier or to increase its immunogenicity.

An alternative approach is to create a fusion protein prepared from an oligonucleotide coding for a C-repeat region segment fused to the 5' end of the CTB gene. For example, oligonucleotides corresponding to the C-repeat region peptides based on the DNA sequence for these regions. The oligonucleotides are fused to the 5' end of the CTB gene by the method described by Dertzbaugh et al, 1990, Infect. Immun. 58:70–79. The CTB-fusion product is expressed in *E. coli* using a system similar to that used by Dertzbaugh et al. 1990, Infect. Immun. 58:70–79. This method eliminates the need to first synthesize the peptide and link it to the CTB molecule.

The presently preferred polypeptides of this invention are:
(1) Ser-Lys-Gln-Asp-Ile-Gly-Ala-Leu-Lys-Gln-Glu-Leu-Ala-Lys-Lys-Asp-Glu-Gly-Asn-Lys
(2) Leu-Asp-Ala-Ser-Arg-Glu-Ala-Lys-Lys-Gln-Val-Glu-Lys-Asp-Leu-Ala-Asn-Leu-Thr-Ala-Glu-Leu
(3) Glu-Lys-Gln-Ile-Ser-Asp-Ala-Ser-Arg-Gln
(4) Ser-Arg-Lys-Gly-Leu-Arg-Arg-Asp-Leu-Asp-Ala-Ser-Arg-Glu-Ala-Lys-Lys-Glu-Val-Glu-Lys
(5) Lys-Glu-Val-Glu-Lys-Asp-Leu-Ala-Asn-Leu-Thr-Ala-Glu-Leu-Asp-Lys-Val-Lys-Glu-Glu-Lys-Glu
(6) Val-Lys-Glu-Glu-Lys-Glu-Ile-Ser-Asp-Ala-Ser-Arg-Glu-Gly-Leu-Arg-Arg-Asp-Leu-Asp-Ala The first peptide will sometimes hereinafter be referred to as peptide 216–235, the second as 248–269, the third as 275–284, the, fourth as 240–260, the fifth as 256–277, and the sixth as 272–292. The numerals refer to the position of the first and the last amino acid residue in the polypeptide as it occurs in the native M protein molecule as it exists on the streptococcal surface, see FIG. 1.

The epitopes represented by these peptides are present in the conserved exposed region of the majority of the known serotypes present in nature. Therefore, if they are shown to raise antibodies against one serotype, they can be expected to have the same response with other serotypes.

The following non-limiting Examples are given by way of illustration only and are not to be considered a limitation of this invention, many apparent variations of which are possible without departing from the spirit or scope thereof.

EXAMPLES

Example 1

Peptides 216–235, 248–269 and 275–284 were synthesized with an additional cysteine residue on the carboxy terminus by the method of Barany and Merrifield. See *The Peptides: Analysis, Synthesis; Biology*. E. Gross and J. Meienhofer, editors. Academic Pressi, Inc. New York, 1–284. They were purified by reverse phase liquid chromatography on a Brownlee C-8 column, eluted as a single peak using a gradient of acetonitrile in 0.1% trifluoroacetic acid and stored in lyophilized form at 4° C. The amino acid sequence was verified both by amino acid composition and sequence determination to the penultimate residue. To eliminate disulfide bridges formed upon storage, several days prior to conjugation to cholera toxin B subunit (CTB) the peptides were reduced with 0.14 M beta-2-mercaptoethanol at pH 7.2 and subjected to several cycles of lyophilization and solubilization to eliminate the reducing agent.

These peptides were used to prepare vaccines for both oral and intranasal immunization of mammals. For the preparation the primary amino groups highly purified CTB in phosphate buffered saline (PBS) were derivatized by addition of a 15 molar excess of the heterobifunctional crossinking agent N'-succinimidyl 3-(-2-pyridyldithio) propionate (SPDP; Pierce Chemical Co., Rockford, Ill.) solubilized in ethanol. The mixture was continuously stirred with a magnetic stirrer until a precipitate formed (about 10 to 15 min).

At this time, the reaction was stopped by addition of ethanolamine to a final concentration of 70 mM, which resulted in immediate clearance of the precipitate. The solution was dialyzed overnight against PBS at 4° C. A small sample of the dialysate was removed and the absorbance at 343 nm was measured before and after addition of 5 mM dithiothreitol to establish the extent of derivatization based on the release of pyridine-2-thione. See Carlson, et al. *Biochem. J.* 173, 723 (1988). Dialyzed CTB was mixed with a single peptide at a 1:1.5. w/w ratio at room temperature for 4 h, then overnight at 4° C. Each of the three individual peptide-CTB conjugates (containing unbound peptide) were pooled in equal weight quantities and aliquots. stored at −80° C. until use. Free peptide was not separated from peptide-CTB conjugates, and the entire mixture containing free. peptide plus linked peptide-CTB was used for immunization. The average number of peptide molecules covalently linked per CTB monomer was calculated based on $A_{343}$ of the mixture (Table 1). This degree of substitution preserved nearly 100% of the CTB binding capacity to $GM_1$ as compared to underivatized CTB (data not shown), determined in a $GM_1$ binding assay (25). See Tsang, et al. *Meth Enz.* 92,391 (1983). Increased substitution of CTB with SPDP led to a marked decrease in $GM_1$ binding capacity.

TABLE 1

| Covalent Linkage of Peptides to CTB. Molar Ratio | |
| --- | --- |
| Peptide | Peptide:CTB (a) |
| 216–235 | 1.12 |
| 248–269 | 1.20 |
| 275–284 | 1.14 |

(a) Molar ratio peptide to CTB in covalently linked form based on pyridine-2-thione release measured at 343 nm.

To determine the ability of the selected peptides and their conjugates to elicit an immunological response in mammals, mice were immunized intranasally (i.n.) 3 times over a 6 day period with the vaccine prepared as described above. Control mice were treated with CTB alone. The animals were rested 3 weeks and boosted i.n. with a single dose of antigen. Each dose contained 20 ug of CTB with or without a total of 12 ug of each peptide. The quantity of peptide indicated represents the total of free and covalently bound product. The vaccine was delivered to the nares of unanesthetized mice (10 ul per nostril) through a Hamilton syringe (model 750) fitted with a repeating dispenser (PB600) and a blunt end needle. Female outbred Swiss CD1 mice (Charles River) were 4 to 5 weeks of age at the onset of immunization.

The same composition may be administered directly into the oral cavity.

Type 6 streptococci (strain S43/192 from The Rockefeller University collection) were used to challenge the vaccinated mice. The strain was selected for resistance to 200 ug/ml streptomycin. Mouse virulence of S43/192 was maintained by several intraperitoneal passages as described by Becker, C. G. Am. J. Pathol. (1964) 44, 51–60. A single stock of organisms was prepared from an overnight culture, concentrated 10-fold, frozen at 80° C., and used for all challenge experiments. Stocks were diluted 1:500 and grown overnight at 37° C. in Todd-Hewitt broth, then diluted 1:20 in fresh growth medium. When cultures reached an $OD_{650}$ of 0.5 (18 mm tube), they were centrifuged and resuspended in saline to one-sixth the volume (approximately $2.5 \times 10^8$ colony forming units or "CFU" per ml). A peptide-CTB vaccinated group of mice was compared to a control group (CTB only) in four separate challenges with live streptococci. In each challenge experiment, the peptide-immunized and control groups contained 12 to 14 mice apiece. At 10 days following boost, mice were administered 10 ul per nostril of the streptococcal suspension. Beginning 24 h after challenge, and at 24 or 48 h intervals thereafter, throats were swabbed (Calgiswab type 4, Spectrum) and cultured on blood agar plates containing 200 ug/ml streptomycin. Cultures were grown overnight at 37° C. and scored for the presence of beta-hemolytic streptococci.

The throat cultures taken at 24 or 48 hour intervals and colonization of streptococci was assessed. The results of four separate challenges are summarized in Table 2. Animals which had, received the peptide-CTB vaccine displayed a decrease in the incidence of pharyngeal infection (plus mortality) during the 10 day following streptococcal challenge. The difference in colonization between peptide-immunized mice and the control group was significant for five of the six time points at which pharyngeal cultures was taken. Furthermore, at every throat culture analysis in each of the four separate challenged experiments, the number of positive throat cultures among the control group exceeded that of the peptide-CTB immunized group 96% of the time (23/24 analyses).

TABLE 2

Protective Immunity Induced by Conserved Synthetic Peptides (a)

| Day Post Challenge | CTB Only | Conserved Peptide-CTB | P-value (b) |
| --- | --- | --- | --- |
| 1 | 23/52 (44%) | 11/52 (21%) | P < 0.025 * |
| 2 | 23/52 (44) | 11/52 (21) | P < 0.025 * |
| 4 | 22/52 (42) | 14/52 (27) | NS |
| 6 | 31/52 (60) | 18/52 (35) | P < 0.025 * |
| 8 | 33/52 (60) | 22/52 (42) | P < 0.050 * |
| 9 & 10 | 33/52 (63) | 22/52 (42) | P < 0.050 * |

(a) Animals were immunized with peptide-CTB conjugates or CTB only, and challenged with live streptococci in four separate experiments. Mice which died during the course of the experiment were scored as positive. The overall mortality rate was 20%, and was not significantly different for the two groups.
(b) P values less than 0.05 (*) were considered to be statistically significant (chi-square analysis). NS, not significant.

The majority of individual mice displayed one of two patterns of pharyngeal colonization. Fifty-seven percent of survivors which had received CTB only, and 76% of peptide-CTB immunized mice, either remained completely free of streptococci at each throat culture, or carried 25 or more colony forming units for nearly all cultures. The remainder of the survivors typically had positive throat cultures at one or two time points only, and 77% of these cultures showed fewer than 10 colonies. Thus, the method for analyzing pharyngeal infection is highly reproducible, and most animals were in either a stable state of streptococcal carriage or organism-free. It is apparent thus that the polypeptides of this invention are capable of eliciting a protective response to streptococcal colonization in mammals by intranasal administration of an effective dose. The individual antigens may be similarly employed. The actual dosage may vary somewhat, but will generally be of the same order of magnitude as similar vaccines. Similar results are achieved by other methods of administering the vaccine, e.g., oral administration.

Example 2

Using the procedure set forth in Example 1, polypeptides 248–269, 240–260, 256–277 and 272–292 were synthesized with an additional cystein residue at the carboxy terminus by solid-phase synthesis. These polypeptides are all within the C repeat region of the M protein of type 6 streptococci (strain 471). The polypeptides were purified by HPLC. Highly purified CTB (Institute Merieux) largely in pentameric from was derivatized at primary amino groups with the heterobifunctional cross-linking agent N'-succinimidyl 3-(2-pyridyldithio) propionate (SPDP; Pierce Chemical Co., Rockford, Ill.) according to the procedure set forth in Bessen, D. and Fischetti, V. A., 1988, *Infect. Immun.* 56:2666–2672, incorporated herein by reference.

The synthetic peptides were mixed with SPDP-derivatized CTB at a 1.5:1 (w/w) ratio. An average of 1.06 to 1.27 peptide molecules were covalently linked per. CTB monomoer, and this degree of substitution preserved nearly all $GM_1$ binding capacity as compared to underivatized CTB. Free peptide was not separated from peptide-CTB conjugates. For the peptide vaccine, a mixture containing equal quantities of each of the four peptide-CTB conjugates was prepared and adjusted to 1.0 mg of CTB per ml. The control groups received underivatized CTB at a concentration of 1 mg/ml. In two separate runs, mice were immunized with the peptide-CTB vaccine or with CTB alone and challenged with type 14 streptococci as follows: Four week old outbred mice (female, Swiss CD1; Charles River) were immunized with either the peptide-CTB mixture (vaccinated group) or CTB alone (control group), three times over a 6-day period. Each dose consisted of 10 ul per nostril and 20 ul oral, and was delivered to unanesthetized animals through a blunt-end needle (see Bessen and Fischetti, *Infect. Immun.*, supra). Animals were given a single booster dose after a three week rest period.

The mice were challenged with type 14 streptococci (strain T14/46/8R) ten days following the boost. This strain was chosen among several other heterologous M types based on its ability to colonize the mouse. Note that the sequence of the M protein for type 14 streptococci is not presently known.

For 18 hours prior to challenge, animals were provided with a 5 g/L solution of streptomycin sulfate in their drinking water (see McCormick et al, 1988, *Infect. Immun.*, 56:2209–22). Streptococci were made resistant to 200 ug of streptomycin per ml, and mouse virulence was maintained by several i.p. passages (see Bessen and Fischetti, supra; Lancefield, 1962, *J. Immunol.* 89:307–313, incorporated herein by reference). Organisms were prepared for challenge as described above (see also Bessen and Fischetti; supra); each mouse received 10 ul/nostril of freshly grown T14/46 streptococci at a concentration of $2.5 \times 10^9$ CFU/ml. Animals were housed four or five per cage with members of the same group, and throats were swabbed 24 h after challenge and for 1 to 3' day intervals thereafter until day 10. Throat swabs were cultured on blood agar plates containing 200 ug/ml streptomycin, and were scored for beta-hemolytic colonies.

It is noted that it is best to use mice that are less than 10 to 12 weeks of age for streptococcal challenge. Older, nonimmune animals seem to be refractory to pharyngeal colonization by the group A streptococcal strains.

The animals which received the peptide-CTB vaccine displayed substantially lower levels of infection than the control group. It is noted that seven additional animals were immunized with CTB only in this Example (Run 2); however, all became pregnant and gave birth between the time of boost and streptococcal challenge, and were therefore considered not to be comparable controls. Interestingly, none of the seven mothers had a positive throat cullture during the entire 10 d follow-up period (data not shown in Table 3). This is in contrast to 100% (8/8) colonization among the normal control group. The combined results of the two runs indicate that the difference between the vaccinated and control groups highly significant for days 2 to 10 (P<0.005). Results are set forth in Table 3.

TABLE 3

Pharyngeal colonization of mice following i.n. challenge with strain T14/46 group A streptococci.

| Days Post-Challenge | No. of mice colonized and dead/total (%)[a] | |
| --- | --- | --- |
| | CTB Only | Peptide-CTB |
| Run 1: | | |
| 1 | 3/15 (20) | 1/16 (6) |
| 2 | 2/15 (13) | 1/16 (6) |
| 3 | 4/15 (27) | 0/16 (0) |
| 6 | 5/15 (33) | 0/16 (0) |
| 7 | 6/15 (40) | 0/16 (0) |
| 9 | 6/15 (40) | 0/16 (0) |
| 10 | 6/15 (40) | 0/16 (0) |
| Run 2: | | |
| 1 | 3/8 (38) | 1/16 (6) |
| 2 | 6/8 (75) | 2/16 (13) |
| 3 | 5/8 (63) | 2/16 (13) |
| 6 | 8/8 (100) | 3/16 (20) |
| 8 | 8/8 (100) | 4/16 (25) |
| 10 | 8/8 (100) | 4/16 (25) |

[a]Statistical difference was highly significant (P < 0.005) for combined data from the two runs on day 2 through day 10, according to chi-square analysis. The number of dead animals recorded by day 10 was as follows: 2, CTB only (Run 1); 0, peptide-CTB (Run 1); 3, CTB only (Run 2); 1, peptide-CTB (Run 2).

This Example shows that the polypeptides and vaccines of this invention are not serotype specific (see also Example 4, infra)

Example 3

Antisera was raised in rabbits to each of the four peptides of Example 2 when covalently linked to ovalbumin (see Bessen and Fischetti, supra; Jones and Fischetti, 1988, *J. Exp. Med.*, 167: 1114–1123, incorporated herein by reference). Serum IgG fractions were individually obtained by absorption to immobilized Protein A, overnight incubation with rotation at 4° C., and elution with 0.58% glacial acetic acid in saline (v/v) (Goding). The eluant was dialyzed, concentrated, and digested with immobilized papain overnight at 37° C. with rotation (Pierce Chemical Co., Rockford, Ill.) (see Coulter et al 1983, *J. Immunol. Meth.*, 59:199–203, incorporated herein by reference). The papain-digested serum IgG preparation was absorbed to immobilized Protein A as described above, and the "fall through" fraction was collected. The identity of the "fall through" fraction was confirmed as Fab fragments by SDS-PAGE and Western blot immunoblot analysis using anti-rabbit IgG (whole molecule) and anti-rabbit IgG (Fab')$_2$ conjugated to alkaline phosphatase (Cappel, West Chester, Pa.) (see Blake et al, 1983, *Anal. Biochem.* 136:175–179, incorporated herein by reference). Under nonreducing conditions, the "fall through" fraction migrated as a major diffuse band at approximately 38 to 40 kDa, whereas the high molecular weight band representing the undigested molecule was not evident. Affinity-purified antipeptide Fab fragments were prepared by absorption of the Protein A-Sepharose "fall through" fraction to gluterdialdehyde glass beads bearing covalently linked peptide, and elution with 0.1 M glycine at pH 2.1 (see Bessen, Jones and Fischetti, 1989, *J. Exp. Med.*, 169:269–283, incorporated herein by reference).

An antibody absorption assay was performed according to the methods described by Bessen, Jones and Fischetti, 1989, *J. ExP. Med.*, 169:269–283. In brief, heat-killed streptococci were prepared from strains D471 (type 6) and T14/46 (type 14), and their concentrations were adjusted to equivalent $OD_{650}$. For antibody absorption to whole streptococci, organisms were tested at two-fold dilutions in 1% BSA-PBS in a preblocked V-bottomed microtiter plate. Affinity-purified antipeptide Fab fragments was added to each well at concentrations giving half-maximal immunoreactivity to ColiM6 antigen (the product of the emm 6.1 gene cloned in *Escherichia coli*). Plates were sealed, mixed rotated overnight, centrifuged, and the supernatants transferred to flat-bottomed microtiter plates that had been precoated with ColiM6 antigen. Alkaline phosphatase-conjugated anti-rabbit IgG (heavy and light chain specific) was used as the secondary antibody (Sigma). Immunoreactivity was measured by kinetic ELISA (K-ELISA), and all measurements were performed in triplicate. The percentage of antibody bound to heat-killed organisms was calculated based on control samples devoid of streptococci.

Fab fragments were prepared from commercially obtained, nonimmune rabbit IgG (whole molecule; Cappel) as described above. The nonimmune binding by group A streptococci of rabbit IgG (whole molecule), IgG-Fc fragments (Cappel), and IgG-Fab fragments was measured by capture ELISA (see Bessen, Jones and Fischetti, supra; Bessen and Fischetti, 1990, J. Infect. Dis., 161:747–54, incorporated herein by reference). The concentration of IgG and IgG fragments was determined by the BCA assay (Pierce). Heat-killed organisms were incubated with subsaturating quantities of rabbit IgG (200 ng/ml), Fc Fragment (67 ng/ml), or Fab fragment (133 ng/ml), and unabsorbed material was quantitated on microtiter plates coated with affinity-purified anti-rabbit IgG (heavy and light chain specific) antibody (Cappel). Strain 29452 (type 22) was included as a positive control for nonimmune binding of rabbit IgG. The control showed that T14/46: binds both intact rabbit IgG and IgG-Fc fragments, but not rabbit IgG Fab fragments.

This example was to determine whether strain T14/46 shares surface-exposed antigenic epitopes with the C repeat region of strain of type 6 streptococci (strain D471). From this Example, the heterologous T14/46 strain used in the challenge of Example 2 has antigenic epitopes on its surface which correspond to the peptides used for immunization in Example 2. The data also demonstrates that these epitopes are non-type-specific. The results are set forth in Table 4.

TABLE 4

Nonimmune binding of rabbit IgG.

| IgG or fragment | Con-centration | % Bound | | |
|---|---|---|---|---|
| | | T14/46 | 29452 | D471 |
| Rabbit IgG | 200 ng/ml | 41.8 | 87.4 | 1.0 |
| Rabbit IgG-Fc | 67 ng/ml | 31.9 | 39.4 | 2.3 |
| Rabbit IgG-Fab | 133 ng/ml | 6.1 | 1.8 | 3.4 |

Example 4

A bacterial assay was performed according to the methods described in Lancefield, supra, and Bessen and Fischetti, 1988, *J. Exp. Med.*, 167:1945–50, incorporated herein by reference. In brief, whole serum (type-specific or nonopsonic control) (100 ul). was added to early-log phase T14/46 or D471 streptococci in Todd-Hewitt broth (100 ul) and whole heparinized blood (400 ul) from a nonopsonic human donor. Type-specific serum was generated by hyperimmunization of rabbits with whole organisms. The mixture was rotated for 3 h at 37° C., a portion was plated in agar, and viable organisms enumerated by counting CFUs. Data is set forth in Table 5 and expressed as total CFUs.

TABLE 5

Bactericidal Activity of Type-Specific Antibody for Heterologous and Homologous Serotypes

| | | CFUs After Rotation in Human Blood Containing: | | |
|---|---|---|---|---|
| Strain | Inoculum (CFU) | Control | Anti-Type 14 Serum | Anti-Type 6 Serum |
| T14/46 | 28 | 7,200 | <6 | 7,728 |
| T14/46 | 34 | 9,912 | <6 | 9,408 |
| D471 | 57 | >24,000 | >24,000 | <6 |
| D471 | 26 | 7,848 | 6,576 | <6 |

Strain D471 and strain T14/46 are of distinct serotypes. Addition of anti-type 14 serum to whole blood of a nonopsonic donor resulted in killing of T14/46 streptococci, whereas anti-type 6 serum had no bactericidal effect. Anti-type 6 serum was bactericidal for D471 but not for T14/46. The results of the opsonophagocytosis assay confirm that T14/46 is a heterologous M type. Furthermore, the results demonstrate that type-specific serum antibodies are required for bactericidal activity in whole blood. However, as shown by Examples 1 and 2, non-type-specific antibodies are capable of eliciting and do elicit protection at the mucosal level.

It is believed that the C repeat region of the M protein consists of highly conserved C repeat blocks, interspersed by spacer sequences which may be less highly conserved among different serotypes (see FIG. 3). The highly conserved C1 and C2 repeat blocks are located adjacent to the cell wall, e.g., in type 6 streptococci.

Absorption assays with antipeptide Fabs, indicate that one Class I-specific mAb:(10B6) maps to peptide (240–260), whereas the other Class I-specific mAb (10F5) maps to both peptide (240–260) and peptide (272–292). In addition, antipeptide antibodies directed to peptide (240–260) and peptide (272–292) have substantial immunoreactivity with the extracted forms of several Class II M proteins on Western blot, although antipeptide antibodies to peptide (248–269) and peptide (256–277) may be to Class I-specific. Thus, within a narrow region of the C repeat region of M6 protein, there may be both Class I-specific and shared antigenic determinants. Therefore, a vaccine consisting of antigens corresponding to the C repeat region will protect against both Class I and Class II streptococci. Thus, preferred polypeptides are the same as or are substantially similar to the sequence of the C repeat region or a portion thereof.

Vaccines for use to protect against streptococcal infection have been proposed previously. These vaccines have been prepared from polypeptides from the hypervariable amino end of the molecule. They have enjoyed some success in providing type specific immunity against homologous serotypes. Their performance has been improved by incorporating several type specific determinants in the same multivalent vaccine. However, given the enormous array of existing M serotypes, this procedure is not an attractive one.

The carrier described above is CTB. Those skilled in the art will recognize that other carriers can be employed. These include, for example, the E. coli labile toxin B subunit or the pili from E. coli cells identified as K99 pili and 987P pili described by Aizpurua and Russell-Jones in *J. Exp. Med.* 167, 440 (1988). The antigen need not be actually joined to the carrier. The two may be coadministered to achieve substantially the same effect.

Other natural carriers which can be employed in the practice of this invention, especially for parenteral administration include tetanus toxoid, keyhold limpet hemocyamin, bovine serum albumin or ovalbumin. Synthetic carriers are also known and can be employed.

The vaccines of this invention may be administered parenterally in an emulsion with various adjuvants. The adjuvants aid in attaining a more durable and higher level of immunity using smaller amounts of antigen in fewer doses than if the immunogen were administered alone. Examples of adjuvants include Freund's adjuvant (complete or incomplete), Adjuvant 65 (containing peanut oil, mannide monooleate and aluminum monostearate and mineral gels such as aluminun hydroxide, aluminum phosphate, or alum. Freund's adjuvant is no longer used in vaccine formulations for humans or for food animals because it contains nonmetabolizable mineral oil and is a potential carcinogen; however, the mineral gels are widely used in commercial veterinary vaccines.

Having thus described in detail preferred embodiments of the present invention, it is to be understood that the invention defined by the appended claims is not to be limited by particular details set forth in the above description as many apparent variations thereof are possible without departing from the spirit or scope of the present invention.

What is claimed is:

1. An antigen conjugate which comprises a linkable carrier covalently bound to a polypeptide which consists of five or more amino acid residues from the conserved exposed region of the M protein of group A streptococci, wherein said antigen conjugate elicits a protective immune response to streptococcal infection in a mammal when administered mucosally.

2. An antigen conjugate of claim 1 wherein said polypeptide consists of five or more amino acid residues from position 235 to position 299 of the conserved exposed region of the M protein of group A streptococci.

3. The antigen conjugate of claim 1 wherein said polypeptide consists of five or more amino acid residues from the C repeat region of the conserved exposed region of the M protein of group A streptococci.

4. The antigen conjugate of claim 1 wherein said polypeptide consists of five or more amino acid residues from the C1 repeat block or the C2 repeat block of the conserved exposed region of the M protein of group A streptococci.

5. The antigen conjugate of claim 1 wherein the amino acid sequence of said polypeptide is selected from the group consisting of:
Ser-Lys-Gln-Asp-Ile-Gly-Ala-Leu-Lys-Gln-Glu-Leu-Ala-Lys-Lys-Asp-Glu-Gly-Asn-Lys;
Leu-Asp-Ala-Ser-Arg-Glu-Ala-Lys-Lys-Gln-Val-Glu-Lys-Asp-Leu-Ala-Asn-Leu-Thr-Ala-Glu-Leu;
Glu-Lys-Gln-Ile-Ser-Asp-Ala-Ser-Arg-Gln;
Ser-Arg-Lys-Gly-Leu-Arg-Arg-Asp-Leu-Asp-Ala-Ser-Arg-Glu-Ala-Lys-Lys-Gln-Val-Glu-Lys;
Lys-Gln-Val-Glu-Lys-Asp-Leu-Ala-Asn-Leu-Thr-Ala-Glu-Leu-Asp-Lys-Val-Lys-Glu-Glu-Lys-Glu; and
Val-Lys-Gln-Glu-Lys-Gln-Ile-Ser-Asp-Ala-Ser-Arg-Gln-Gly-Leu-Arg-Arg-Asp-Leu-Asp-Ala.

6. The antigen conjugate of claim 1 wherein said carrier comprises a natural protein carrier.

7. The antigen conjugate of claim 1 wherein said carrier comprises cholera toxin B.

8. A mucosal vaccine to protect against streptococcal infection which comprises a biologically acceptable diluent and the antigen conjugate of claim 1; said conjugate being present in an amount which is sufficient to stimulate the production of an immune response following mucosal administration sufficient to elicit such protection.

9. A method of controlling streptococcal infection in a mammal in need of such control which comprises mucosal administration to said mammal of an antigen conjugate of claim 1 in an amount that is sufficient to stimulate the production of a streptococcal infection controlling immune response.

10. The antigen conjugate of claim 1, wherein the amino acid sequence consists of ten or more amino acid residues from the conserved exposed region of the M protein of group A streptococci.

11. The antigen conjugate of claim 1, wherein the amino acid sequence consists of ten to 22 amino acid residues from the conserved exposed region of the M protein of group A streptococci.

* * * * *

UNITED STATES PATENT AND TRADEMARK OFFICE
CERTIFICATE OF CORRECTION

PATENT NO. : 6,602,507 B1
DATED : August 5, 2003
INVENTOR(S) : Vincent A. Fischetti It is certified that error appears in the above-identified patent and that said Letters Patent is hereby corrected as shown below:

Column 1,
Line 25, "exists" should read -- exist --

Column 2,
Line 54, "zenotypes" should read -- xenotypes --

Column 5,
Lines 32-33, "(4) Ser-Arg-Lys-Gly-Leu-Arg-Arg-Asp-Leu-Asp-Ala-Ser-Arg-Glu-Ala-Lys-Lys-Glu-Val-Glu-Lys" should read -- (4) Ser-Arg-Lys-Gly-Leu-Arg-Arg-Asp-Leu-Asp-Ala-Ser-Arg-Glu-Ala-Lys-Lys-Gln-Val-Glu-Lys --;
Lines 34-35, "(5) Lys-Glu-Val-Glu-Lys-Asp-Leu-Ala-Asn-Leu-Thr-Ala-Glu-Leu-Asp-Lys-Val-Lys-Glu-Glu-Lys-Glu" should read
-- (5) Lys-Gln-Val-Glu-Lys-Asp-Leu-Ala-Asn-Leu-Thr-Ala-Glu-Leu-Asp-Lys-Val-Lys-Glu-Glu-Lys-Gln --;
Lines 36-37, "(6) Val-Lys-Glu-Glu-Lys-Glu-Ile-Ser-Asp-Ala-Ser-Arg-Glu-Gly-Leu-Arg-Arg-Asp-Leu-Asp-Ala" should read -- (6) Val-Lys-Glu-Glu-Lys-Gln-Ile-Ser-Asp-Ala-Ser-Arg-Gln-Gly-Leu-Arg-Arg-Asp-Leu-Asp-Ala --

Column 6,
Line 10, insert -- of -- after "groups";
Line 32, delete "." after "free"

Column 7,
Line 10, "80° C" should read -- -80° C --;
Line 30, delete "," after "had"

Column 8,
Line 18, "cystein" should read -- cysteine --

Column 9,
Line 3, delete "'"

Column 10,
Line 22, "*ExP.*" should read -- *Exp.* --;
Line 28, "was" should read -- were --

Column 12,
Line 1, delete "to";
Line 9, "for use to protect" should read -- for protection --

UNITED STATES PATENT AND TRADEMARK OFFICE
CERTIFICATE OF CORRECTION

PATENT NO. : 6,602,507 B1
DATED : August 5, 2003
INVENTOR(S) : Vincent A. Fischetti It is certified that error appears in the above-identified patent and that said Letters Patent is hereby corrected as shown below:

Column 13,
Lines 11-12, "Lys-Gln-Val-Glu-Lys-Asp-Leu-Ala-Asn-Leu-Thr-Ala-Glu-Leu-Asp-Lys-Val-Lys-Glu-Glu-Lys-Glu" should read -- Lys-Gln-Val-Glu-Lys-Asp-Leu-Ala-Asn-Leu-Thr-Ala-Glu-Leu-Asp-Lys-Val-Lys-Glu-Glu-Lys-Gln --
Lines 13-14, "Val-Lys-Gln-Glu-Lys-Gln-Ile-Ser-Asp-Ala-Ser-Arg-Gln-Gly-Leu-Arg-Arg-Asp-Leu-Asp-Ala" should read -- Val-Lys-Glu-Glu-Lys-Gln-Ile-Ser-Asp-Ala-Ser-Arg-Gln-Gly-Leu-Arg-Arg-Asp-Leu-Asp-Ala --

Signed and Sealed this

Twenty-third Day of December, 2003

JAMES E. ROGAN
*Director of the United States Patent and Trademark Office*